(12) United States Patent
Rochling et al.

(10) Patent No.: US 7,655,599 B2
(45) Date of Patent: Feb. 2, 2010

(54) AGROCHEMICAL FORMULATIONS

(75) Inventors: Andreas Rochling, Langenfeld (DE); Frank Rosenfeldt, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 356 days.

(21) Appl. No.: 10/563,328

(22) PCT Filed: Jun. 21, 2004

(86) PCT No.: PCT/EP2004/006673

§ 371 (c)(1), (2), (4) Date: Dec. 30, 2005

(87) PCT Pub. No.: WO2005/002334

PCT Pub. Date: Jan. 13, 2005

(65) Prior Publication Data

US 2006/0183639 A1    Aug. 17, 2006

(30) Foreign Application Priority Data

Jul. 2, 2003 (DE) .................. 103 29 714

(51) Int. Cl.
*A01N 43/72* (2006.01)
*A01N 43/653* (2006.01)
*A01N 37/44* (2006.01)

(52) U.S. Cl. .............. 504/223; 504/273; 504/315; 514/229.2; 514/383; 514/538

(58) Field of Classification Search ............ 504/116, 504/223, 273, 315; 514/229.2, 383, 538
See application file for complete search history.

(56) References Cited

U.S. PATENT DOCUMENTS

| | | | |
|---|---|---|---|
| 4,415,355 A | | 11/1983 | Cassell et al. |
| 5,279,766 A | * | 1/1994 | Dahms .................. 516/55 |
| 5,476,845 A | | 12/1995 | Reizlein et al. |
| 5,597,840 A | | 1/1997 | Moore |
| 5,705,476 A | | 1/1998 | Hoffarth |
| 5,731,264 A | | 3/1998 | Narayanan et al. |
| 6,248,695 B1 | * | 6/2001 | Griffiths et al. ............ 504/206 |
| 6,277,856 B1 | * | 8/2001 | Cotter et al. ........... 514/259.31 |
| 6,602,823 B1 | | 8/2003 | Röchling et al. |
| 2003/0083201 A1 | | 5/2003 | Kobayashi |

FOREIGN PATENT DOCUMENTS

| | | |
|---|---|---|
| EP | 0 235 773 A1 | 9/1987 |
| EP | 0 281 810 A1 | 9/1988 |
| EP | 0 655 197 A1 | 5/1995 |
| EP | 0 681 865 A2 | 11/1995 |
| EP | 0 933 025 A1 | 8/1999 |
| EP | 1 023 837 A2 | 8/2000 |
| EP | 1 025 757 A1 | 8/2000 |
| WO | WO 88/06406 A1 | 9/1988 |
| WO | WO 98/35553 A1 | 8/1998 |
| WO | WO 99/65301 A1 | 12/1999 |
| WO | WO 00/35278 A1 | 6/2000 |
| WO | WO 02/091828 A1 | 11/2002 |
| WO | WO 03/037084 A1 * | 5/2003 |
| WO | WO04000022 A1 * | 12/2003 |

OTHER PUBLICATIONS

Dutzmann, S, HEC5725: A Novel Leaf-Systemic Strobilurin Fungicide, (2002), BCPC Conference—Pests and Diseases, vol. 1, Abstract.*
Lianyou Products list [online]. Aug. 2003, retrieved from Internet Mar. 2, 2009: ,URL: <http://web.archive.org/web/20030812172430/ http://www.friendsunion.com/product-4-e.htm>, pp. 1-2.*
Dutzmann, S., et al., "HEC5725: A novel leaf-systemic strobilurin fungicide," *The BCPC Conference: Pests & Diseases* 1:365-370, British Crop Protection Council (Nov. 2002).
International Search Report for International Application No. PCT/EP2004/006673, European Patent Office, Netherlands, mailed Nov. 24, 2004.

* cited by examiner

*Primary Examiner*—Johann R Richter
*Assistant Examiner*—Andriae M Holt
(74) *Attorney, Agent, or Firm*—Sterne, Kessler, Goldstein & Fox P.L.L.C.

(57) ABSTRACT

The present invention relates to novel agrochemical formulations based on ethylene diamine alkoxylate derivative emulsifiers, to a method for producing said formulations, and to the use of the same for applying the active ingredients contained therein.

6 Claims, No Drawings

AGROCHEMICAL FORMULATIONS

This application is a National Stage of International Application No. PCT/EP2004/06673, filed Jun. 21, 2004, which claims the benefit of DE 10329714.6, filed Jul. 2, 2003. The entirety of each of these applications is incorporated by reference herein.

The present invention relates to novel agrochemical formulations based on ethylene diamine alkoxylate derivative emulsifiers, to a method for producing said formulations, and to the use of the same for applying the active ingredients contained therein.

Many formulations of plant protection products are known, in which an active ingredient that is not soluble in water is contained in the emulsifiable concentrate (EC formulation) together with a solvent that is soluble in water. Examples of solvents that are used for an active ingredient are N-methylpyrrolidone (NMP) and dimethyl sulfoxide (DMSO).

When the concentrate is used it is diluted with water.

A disadvantage of the known formulations is that, in use, both the water-soluble solvent diffuses into the water, and water diffuses into the emulsifiable oil droplets consisting of solvent and active material. This destabilises the suspension or emulsion, and the active ingredient crystallises out of the aqueous ready-to-use emulsion or suspension (spray liquor).

It was now the object of the present invention to find a formulation, which enables the aqueous ready-to-use emulsion or suspension to be diluted with water, without the active ingredient crystallising out.

Novel agrochemical formulations were now found, which contain
a) at least one agrochemical active ingredient,
b) if necessary, a penetration promoter,
c) if necessary, an emulsifier,
d) if necessary, additives,
e) γ-butyrolactone and
f) at least one compound, which acts as an emulsion stabiliser and/or as a crystallisation inhibitor.

Furthermore, it was found that the agrochemical formulations according to the invention can be produced by mixing
at least one agrochemical active ingredient,
if necessary, with a penetration promoter,
if necessary, with an emulsifier,
if necessary, with additives,
γ-butyrolactone and with
a compound, which acts as an emulsion stabiliser and/or as a crystallisation inhibitor.

Finally, it was found that the agrochemical formulations according to the invention are very well suited for applying the active ingredients contained therein to plants and/or to their habitat.

It is extremely surprising to note that, unlike known formulations, the formulations according to the invention do not crystallise out. In particular, the presence of γ-butyrolactone as a solvent, and of ethylene diamine alkoxylate derivatives, such as Synperonic T/304®, for example, as an emulsion stabiliser and crystallisation inhibitor, prevents the active ingredients in the spray liquor from crystallising out.

As well as the advantage that, in the formulations according to the invention, active ingredients with very low solubility in water exhibit a reduced tendency to crystallise when diluted with water, the formulations according to the invention are characterised by a series of further advantages. Accordingly, only very low foaming occurs when the formulations according to the invention are mixed with water. Furthermore, the formulations promote the biological effectiveness of the active components contained therein. In addition, with the formulations according to the invention, an improved storage stability is achieved, which it would otherwise not be possible to achieve due to the incompatibility of the active ingredients.

The subject matter of the invention is preferably agrochemical formulations, which contain
a) at least one agrochemical active ingredient,
b) if necessary, a penetration promoter,
c) if necessary, an emulsifier,
d) if necessary, additives,
e) γ-butyrolactone and
f) at least one ethylene diamine alkoxylate derivative.

Especially preferred are agrochemical formulations, which contain
a) at least one agrochemical active ingredient,
b) if necessary, a penetration promoter,
c) if necessary, an emulsifier,
d) if necessary, additives,
e) γ-butyrolactone and
f) Synperonic T/304® having the chemical formula,

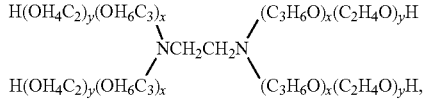

wherein x and y are both 4.

The formulations according to the invention contain one or more agrochemical active ingredients. Here, agrochemical active ingredients are understood to mean all substances commonly used for the treatment of plants. Preferred substances are fungicides, bactericides, insecticides, acaricides, nematicides, herbicides, plant growth regulators, plant nutrients and repellents.

Examples of fungicides are:
2-aminobutane; 2-anilino-4-methyl-6-cyclopropyl-pyrimidine; 2',6'-dibromo-2-methyl-4'-trifluoro-methoxy-4'-trifluoromethyl-1,3-thiazole-5-carboxanilide; 2,6-dichloro-N-(4-trifluoromethylbenzyl)-benzamide; (E)-2-methoximino-N-methyl-2-(2-phenoxyphenyl)acetamide; 8-hydroxy-chinolin sulphate; methyl-(E)-2-{2-[6-(2-cyanophenoxy)-pyrimidin-4-yloxy]-phenyl}-3-methoxyacrylate; methyl-(E)-methoximino[alpha-(o-tolyloxy)-o-tolyl]-acetate; 2-phenylphenol (OPP), Aldimorph, Ampropylfos, Anilazine, Azaconazole, Benalaxyl, Benodanil, Benomyl, Binapacryl, Biphenyl, Bitertanol, Blasticidin-S, Bromuconazole, Bupirimate, Buthiobate, Calcium polysulphide, Captafol, Captan, Carbendazim, Carboxin, Chinomethionate (Quinomethionate), Chloroneb, Chloropicrin, Chlorothalonil, Chlozolinate, Cufraneb, Cymoxanil, Cyproconazole, Cyprofuram, Dichlorophen, Diclobutrazol, Dichlofluanid, Diclomezin, Dicloran, Diethofencarb, Difenoconazole, Dimethirimol, Dimethomorph, Diniconazole, Dinocap, Diphenylamin, Dipyrithion, Ditalimfos, Dithianone, Dodine, Drazoxolon, Edifenphos, Epoxyconazole, Ethirimol, Etridiazole, Fenarimol, Fenbuconazole, Fenfuram, Fenitropan, Fenpiclonil, Fenpropidin, Fenpropimorph, Fentin acetate, Fentin hydroxide, Ferbam, Ferimzone, Fluazinam, Fludioxonil, Fluoromide, Fluquinconazole, Flusilazole, Flusulfamide, Flutolanil, Flutriafol, Folpet, Fosetyl-Aluminium, Fthalide, Fuberidazole, Furalaxyl, Furmecyclox, Guazatine, Hexachlorobenzene, Hexaconazole, Hymexazol, Imazalil, Imibenconazole, Iminoctadine, Iprobenfos (IBP), Iprodione, Isoprothiolane, Kasugamycin, Mancozeb, Maneb, Mepanipyrim, Mepronil, Metalaxyl, Metconazole, Methasulfocarb, Methfuroxam, Metiram, Metsulfovax, Myclobutanil, Nickel dimethyldithiocarbamate, Nitrothal-isopropyl, Nuarimol, Ofurace, Oxadixyl, Oxamocarb, Oxycarboxin, Pefurazoate, Penconazole, Pencycuron, Phosdiphen, Pimaricin, Piperalin, Polyoxin, Probenazole, Prochloraz, Procymidone, Propamocarb, Propiconazole, Propineb, Pyrazophos, Pyrifenox, Pyrimethanil, Pyroquilon, Quintozene (PCNB), Tebuconazole, Tecloftalam, Tecnazene, Tetraconazole, Thiabendazole, Thicyofen, Thiophanate-methyl, Thiram, Tolclophos-methyl, Tolylfluanid, Triadimefon, Triadimenol, Triazoxide, Trichlamide, Tricyclazole, Tridemorph, Triflumizole, Triforine, Triticonazole, Validamycin A, Vinclozolin, Zineb, Ziram, 8-tert.-butyl-2-(N-ethyl-N-n-propyl-amino)-methyl-1,4-dioxaspiro-[4,5]decan, N-(R)-[1-(4-chlorophenyl)-ethyl]-2,2-dichlor-1-ethyl-3t-methyl-1r-cyclopropane carboxylic acid amide (diastereomeric or individual isomers),

[2-methyl-1-[[[1-(4-methylphenyl)-ethyl]-amino]-carbonyl]-propyl]-carbamic acid-1-methylethylester, 1-methyl-cyclohexyl-1'-carboxylic acid-(2,3-dichlor-4-hydroxy)-anilide, 2-[2-(1'-chloro-cyclopropyl)-3-(2-chlorphenyl)-2-hydroxypropyl]-2,4-dihydro-[1,2,4]-triazol-3-thion, 1-(3,5-dimethyl-isoxazol-4-sulfonyl)-2-chloro-6,6-difluoro-[1,3]-dioxolo-[4,5-f]-benzimidazol and (5,6-dihydro-1,4,2-dioxazin-3-yl)-{2-[[6-(2-chlorophenoxy)-5-fluoro-4-pyrimidinyl]-oxy]phenyl}-methanol-O-methyl oxime.

Examples of bactericides are:

Bronopol, Dichlorophen, Nitrapyrin, Nickel dimethyldithiocarbamate, Kasugamycin, Octhilinone, Furancarboxylic acid, Oxytetracyclin, Probenazole, Streptomycin, Tecloftalam, Copper sulphate and other copper preparations, Examples of insecticides, acaricides and nematicides are:

Abamectin, Acephate, Acrinathrin, Alanycarb, Aldicarb, Alphamethrin, Amitraz, Avermectin, AZ 60541, Azadirachtin, Azinphos A, Azinphos M, Azocyclotin,

*Bacillus thuringiensis*, 4-bromo-2-(4-chlorphenyl)-1-(ethoxymethyl)-5-(trifluoromethyl)-1H-pyrrole-3-carbonitrile, Bendiocarb, Benfuracarb, Bensultap, Beta-cyfluthrin, Bifenthrin, BPMC, Brofenprox, Bromophos A, Bufencarb, Buprofezin, Butocarboxin, Butylpyridaben, Cadusafos, Carbaryl, Carbofuran, Carbophenothion, Carbosulfan, Cartap, Chloethocarb, Chlorethoxyfos, Chlorfenvinphos, Chlorfluazuron, Chlormephos, N-[(6-chloro-3-pyridinyl)-methyl]-N'-cyano-N-methyl-ethanimidamide, Chlorpyrifos, Chlorpyrifos M, Cis-resmethrin, Clocythrin, Clofentezine, Cyanophos, Cycloprothrin, Cyfluthrin, Cyhalothrin, Cyhexatin, Cypermethrin, Cyromazine, Deltamethrin, Demeton-M, Demeton-S, Demeton-S-methyl, Diafenthiuron, Diazinon, Dichlofenthion, Dichlorvos, Dicliphos, Dicrotophos, Diethion, Diflubenzuron, Dimethoate, Dimethylvinphos, Dioxathion, Disulfoton, Edifenphos, Emamectin, Esfenvalerate, Ethiofencarb, Ethion, Ethofenprox, Ethoprophos, Etrimphos, Fenamiphos, Fenazaquin, Fenbutatin oxide, Fenitrothion, Fenobucarb, Fenothiocarb, Fenoxycarb, Fenpropathrin, Fenpyrad, Fenpyroximate, Fenthion, Fenvalerate, Fipronil, Fluazinam, Fluazuron, Flucycloxuron, Flucythrinate, Flufenoxuron, Flufenprox, Fluvalinate, Fonophos, Formothion, Fosthiazate, Fubfenprox, Furathiocarb, HCH, Heptenophos, Hexaflumuron, Hexythiazox, Imidacloprid, Iprobenfos, Isazophos, Isofenphos, Isoprocarb, Isoxathion, Ivermectin, Lambda-cyhalothrin, Lufenuron, Malathion, Mecarbam, Mervinphos, Mesulfenphos, Metaldehyde, Methacrifos, Methamidophos, Methidathion, Methiocarb, Methomyl, Metolcarb, Milbemectin, Monocrotophos, Moxidectin, Naled, NC 184, Nitenpyram, Omethoat, Oxamyl, Oxydemethon M, Oxydeprofos, Parathion A, Parathion M, Permethrin, Phenthoate, Phorate, Phosalone, Phosmet, Phosphamidon, Phoxim, Pirimicarb, Pirimiphos M, Pirimiphos A, Profenofos, Promecarb, Propaphos, Propoxur, Prothiophos, Prothoate, Pymetrozin, Pyrachlophos, Pyradaphenthion, Pyresmethrin, Pyrethrum, Pyridaben, Pyrimidifen, Pyriproxifen, Quinalphos, Salithion, Sebufos, Silafluofen, Sulfotep, Sulprofos, Tebufenozide, Tebufenpyrad, Tebupirimphos, Teflubenzuron, Tefluthrin, Temephos, Terbam, Terbufos, Tetrachlorvinphos, Thiafenox, Thiarnethoxam, Thiodicarb, Thiofanox, Thiomethon, Thionazin, Thuringiensin, Tralomethrin, Transfluthrin, Triarathen, Triazophos, Triazuron, Trichlorfon, Triflumuron, Trimethacarb, Vamidothion, XMC, Xylylcarb, Zetamethrin.

Examples of herbicides are:

Anilides, such as Diflufenican and Propanil; Aryl carboxylic acids, such as Dichloropicolinic acid, Dicamba and Picloram; Aryloxyalkanoic acids, such as 2,4-D, 2,4-DB, 2,4-DP, Fluroxypyr, MCPA, MCPP and Triclopyr; Aryloxyphenoxy-alkanoic acid esters, such as Diclofop-methyl, Fenoxaprop-ethyl, Fluazifop-butyl, Haloxyfop-methyl and Quizalofop-ethyl; Azinones, such as Chloridazon and Norflurazon; Carbamates, such as Chlorpropham, Desmedipham, Phenmedipham and Propham; Chloroacetanilides, such as Alachlor, Acetochlor, Butachlor, Metazachlor, Metolachlor, Pretilachlor and Propachlor; Dinitroanilines, such as Oryzalin, Pendimethalin and Trifluralin; Diphenylethers, such as Acifluorfen, Bifenox, Fluoroglycofen, Fomesafen, Halosafen, Lactofen and Oxyfluorfen; Ureas, such as Chlortoluron, Diuron, Fluometuron, Isoproturon, Linuron and Methabenzthiazuron; Hydroxylamines, such as Alloxydim, Clethodim, Cycloxydim, Sethoxydim and Tralkoxydim; Imidazolinones, such as Imazethapyr, Imazamethabenz, Imazapyr and Imazaquin; Nitriles, such as Bromoxynil, Dichlobenil and Ioxynil; Oxyacetamides, such as Mefenacet; Sulfonyl ureas, such as Amidosulfuron, Bensulfuron-methyl, Chloroimuron-ethyl, Chlorsulfuron, Cinosulfuron, Metsulfuron-methyl, Nicosulfuron, Primisulfuron, Pyrazosulfuron-ethyl, Thifensulfuron-methyl, Triasulfuron and Tribenuron-methyl; Thiolcarbamates, such as Butylate, Cycloate, Diallate, EPTC, Esprocarb, Molinate, Prosulfocarb, Thiobencarb and Triallate; Triazines, such as Atrazine, Cyanazine, Simazine, Simetryne, Terbutryne and Terbuthylazine; Triazinones, such as Hexazinone, Metamitron and Metribuzin; Others, such as Aminotriazol, 4-amino-N-(1,1-dimethylethyl)-4,5-dihydro-3-(1-methylethyl)-5-oxo-1H-1,2,4-triazole-1-carboxamide, Benfuresate, Bentazone, Cinmethylin, Clomazone, Clopyralid, Difenzoquat, Dithiopyr, Ethofumesate, Fluorochloridone, Glufosinate, Glyphosate, Isoxaben, Pyridate, Quinchlorac, Quinmerac, Sulphosate and Tridiphane.

Examples of plant growth regulators are Chlorcholinchloride and Ethephon

Examples of plant nutrients are common inorganic or organic fertilisers for providing plants with macro and/or micro nutrients.

Examples of repellents are Diethyltolylamide, Ethyl hexanediol and Butopyronoxyl.

Preferred examples of fungicides are the Strobilurin fungicides, such as

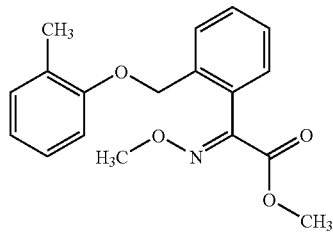

(Kresoxim-methyl)

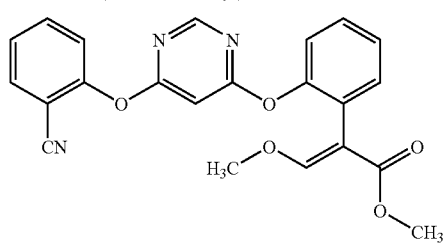

(Azoxystrobin)

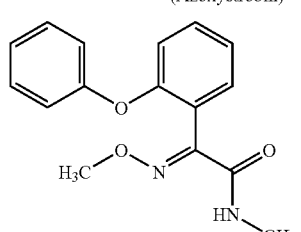

(Metominostrobin)

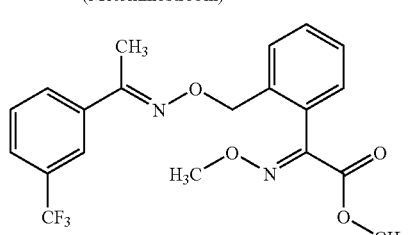

(Trifloxystrobin)

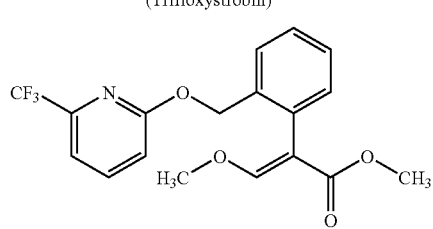

(Picoxystrobin)

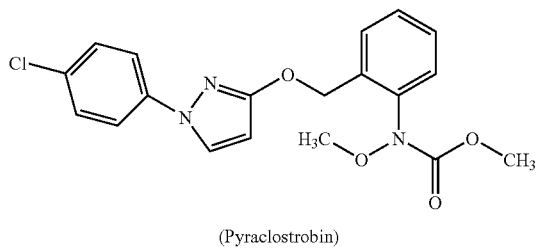

(Pyraclostrobin)

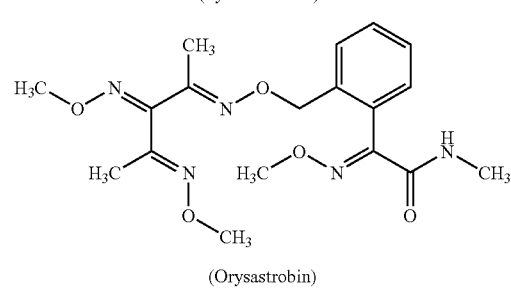

(Orysastrobin)

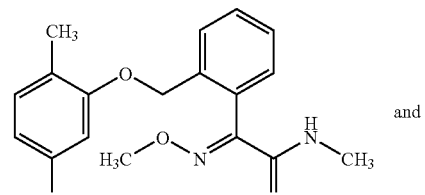

and

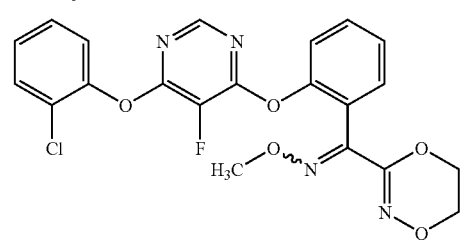

(Fluoxastrobin)

as well as the azole fungicides, such as

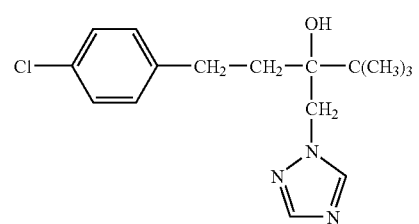

(Tebuconazole)

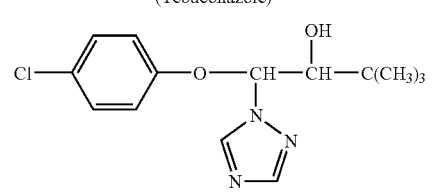

(Triadimenol)

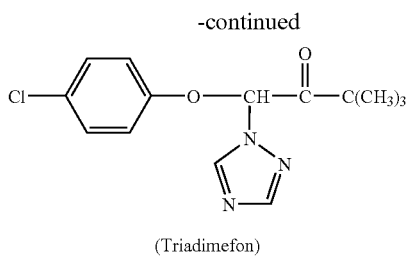

(Triadimefon)

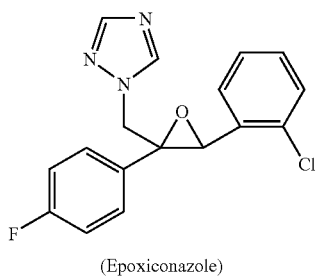

(Epoxiconazole)

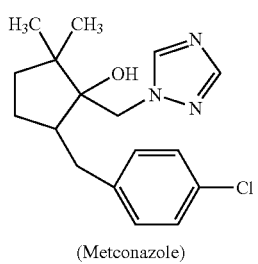

(Metconazole)

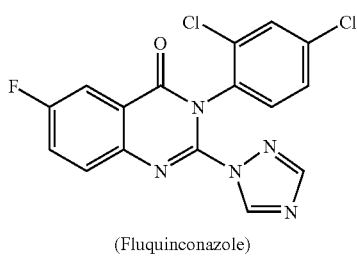

(Fluquinconazole)

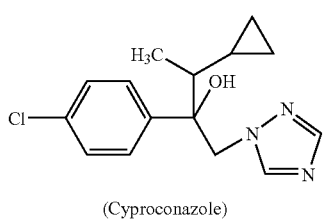

(Cyproconazole)

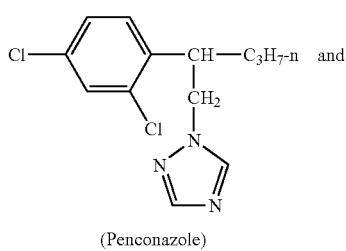

(Penconazole)

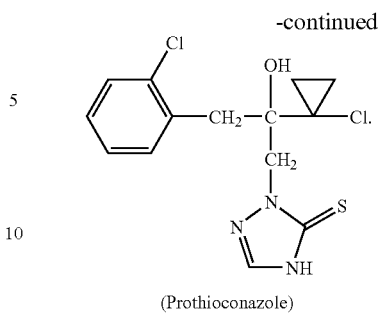

(Prothioconazole)

Preferred examples of fungicides are Prothioconazole, Fluoxastrobin und Trifloxystrobin.

Prothioconazole and Fluoxastrobin are particularly preferred.

Furthermore the formulations according to the invention also contain penetration promoters if necessary. In the present context, all those substances, which are commonly used to improve the penetration of agrochemical active ingredients in plants, are suitable for use as penetration promoters.

Preferred are alkanol-alkoxylates according to the formula $$R\text{—}O\text{-}(\text{-}AO)_m H \qquad (I)$$

in which

R represents straight-chained or branched alkyl with 4 to 20 carbon atoms,

AO represents an ethylene oxide remainder, a propylene oxide remainder, a butylene oxide remainder or mixtures of ethylene oxide and propylene oxide remainders, and m represents numbers from 2 to 30.

A particularly preferred group of penetration promoters are alkanol alkoxylates according to the formula $$R\text{—}O\text{-}(\text{-}EO\text{—})_n\text{—}H \qquad (Ia)$$

in which

R has the same meaning as above,

EO represents —$CH_2$—$CH_2$—O—, and n represents numbers from 2 to 20.

A further particularly preferred group of penetration promoters are alkanol alkoxylates according to the formula $$R\text{—}O\text{-}(\text{-}EO\text{—})_p\text{—}(\text{—}PO\text{—})_q\text{—}H \qquad (Ib)$$

in which

R has the same meaning as above,

EO represents —$CH_2$—$CH_2$—O—, and

PO represents $$\text{—}CH_2\text{—}\underset{\underset{CH_3}{|}}{CH}\text{—}O\text{—},$$

p represents numbers from 1 to 10, and q represents numbers from 1 to 10.

A further particularly preferred group of penetration promoters are alkanol alkoxylates according to the formula $$R\text{—}O\text{—}(\text{—}PO\text{—})_r\text{-}(EO\text{—})_s\text{—}H \qquad (Ic)$$

in which

R has the same meaning as above,

EO represents —CH2—CH2-O—, and

PO represents $$\text{—}CH_2\text{—}\underset{\underset{CH_3}{|}}{CH}\text{—}O\text{—},$$

r represents numbers from 1 to 10, and s represents numbers from 1 to 10.

A further particularly preferred group of penetration promoters are alkanol alkoxylates according to the formula

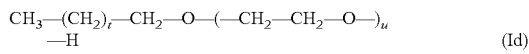 (Id)

in which t represents numbers from 8 to 13.

and u represents numbers from 6 to 17.

In the formulae specified above,

R preferably represents butyl, i-butyl, n-pentyl, i-pentyl, neopentyl, n-hexyl, i-hexyl, n-octyl, i-octyl, 2-ethyl-hexyl, nonyl, i-nonyl, decyl, n-dodecyl, i-dodecyl, lauryl, myristyl, i-tridecyl, trimethyl-nonyl, palmityl, stearyl or eicosyl.

An example of an alkanol alkoxylate according to Formula (Ic) is 2-ethyl-hexyl-alkoxylate according to the formula

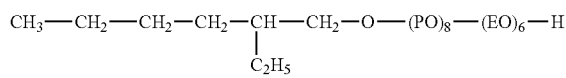 (Ic-1)

in which

EO represents —CH2—CH2—O—,

PO represents

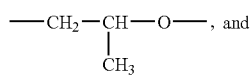, and the numbers 8 and 6 constitute average values.

Particularly preferred alkanol alkoxylates according to Formula (Id) are compounds of this formula, in which t represents numbers from 9 to 12, and u represents numbers from 7 to 9.

Alkanol alkoxylates are defined in general by the above formulae. These substances are mixtures of materials of the specified type with different chain lengths. Average values, which may also be other than whole numbers, are therefore calculated for the indices.

An example is alkanol alkoxylate according to Formula (Id), in which t represents the average value 10.5, and U represents the average value 8.4.

Alkanol alkoxylates according to the specified formulae are known or can be produced by known methods (cf. WO 98-35 553, WO 00-35 278 and EP-A 0 681 865).

All common formulation aids, such as organic solvents, anti-foaming agents, dispersing agents, preservatives, citric acid and its hydrates, colourants, filler materials and even water, are suitable for use as additives, which can be contained in the formulations according to the invention.

Common anti-foaming agents present in formulations of agrochemical active ingredients are suitable for use as anti-foaming agents. Examples are silicone oils, dispersions of silicone oils, magnesium stearate, phosphinic acids and phosphonic acids. Fluowet PL 80® is particularly preferred.

All common organic solvents, which effectively dissolve the agrochemical active ingredients used, are suitable for use as organic solvents. Preferred are aliphatic and aromatic, if necessary halogenated hydrocarbons, such as Toluol, Xylol, Solvesso®, mineral oils, such as white spirit, petroleum, alkyl benzole and spindle oil, also tetrachloromethane, chloroform, methylene chloride and dichloromethane, in addition esters, such as ethyl acetate, furthermore lactones, such as butyrolactone, in addition lactames, such as N-methylpyrrolidone, N-octylpyrrolidone and N-methylcaprolactam, and also alkanoic carboxylic acid amides, such as decanecarboxylic acid di-methylamide and octanecarboxylic acid dimethylamide, as well as dimethylformamide. Water-soluble solvents, such as N-methylpyrrolidone und DMSO, are preferred. γ-butyrolactone is particularly preferred.

Common surface-active substances present in formulations of agrochemical active ingredients are suitable for use as emulsifiers. Examples are ethoxylated nonylphenols, polyethylene glycol ethers of linear alcohols, conversion products of alkylphenols with ethylene oxide and/or propylene oxide, ethylene oxide-propylene oxide block copolymers, polyethylene glycols and polypropylene glycols, furthermore fatty acid esters, alkyl sulphonates, alkyl sulphates, aryl sulphates, ethoxylated arylalkylphenols, such as tristyryl-phenol-ethoxylate with an average of 16 ethylene oxide units per molecule, furthermore ethoxylated and propoxylated arylalkylphenols as well as sulphated or phosphated arylalkylphenol-ethoxylates or -ethoxy- and -propoxylates. Tristyrylphenol alkoxylates are particularly preferred. Tristyrylphenol ethoxylates together with tristyrylphenol ethoxy propoxylates are especially preferred.

All substances commonly used as dispersing agents in plant protection products are suitable for this purpose. Along with the examples mentioned above under emulsifiers, preferred substances are natural and synthetic, water soluble polymers, such as gelatines, starches and cellulose derivatives, in particular cellulose ester and cellulose ether, furthermore polyvinyl alcohol, poly-vinylpyrrolidon, polyacrylic acid, polymethacrylic acid and co-polymerisates of (meth)acrylic acid and (meth)acrylic acid esters, and, in addition, co-polymerisates of methacrylic acid and methacrylic acid ester neutralised with alkaline metal hydroxide.

All substances commonly used as preservatives in plant treatment products are suitable for this purpose. Examples are Preventol® and Proxel®.

All common inorganic or organic colourants used in the production of plant protection products are suitable for use as colourants. Examples are titanium dioxide, lampblack, zinc oxide and blue pigments.

All substances commonly used as fillers in plant protection products are suitable for this purpose. Preferred substances are inorganic particles, such as carbonates, silicates and oxides, with a medium particle size of 0.005 to 5 µm, particularly preferably from 0.02 to 2 µm. Examples are silicon dioxide, so-called highly dispersible silicic acids, silicic gels, as well as natural and synthetic silicates and alumosilicates.

All substances commonly used as compounds, which act as emulsion stabilisers and/or crystallisation inhibitors, in plant protection products are suitable for this purpose. Ethylene diamine alkoxylate derivatives are preferred. Ethylene diamine alkoxylate with the trade name Synperonic T/304® produced by the company Uniqema is particularly preferred.

The concentration of the individual components in formulations according to the invention can be varied over a larger range. The concentrations of agrochemical active ingredients in general lie between 1 and 40% by weight, preferably between 20 and 30% by weight, of penetration promoters in general lie between 0 and 25% by weight, preferably between 10 and 25% by weight, of emulsifiers in general lie between 5 and 30% by weight, preferably between 10 and 25% by weight, of additives in general lie between 0 and 40% by weight, preferably between 0 and 2% by weight, of compounds, which act as emulsion stabilisers and/or crystallisation inhibitors, in general lie between 5 and 20% by weight, preferably between 5 and 15% by weight, of γ-butyrolactone in general lie between 20 and 70% by weight, preferably between 30 and 50% by weight.

The production of the agrochemical formulations according to the invention is carried out by mixing the components together in the respective ratios required. If the agrochemical active ingredient is a solid substance, then this is generally used either in a finely ground form or in the form of a solution or suspension in an organic solvent. If the agrochemical active ingredient is liquid, then it is often not necessary to use an organic solvent. It is also possible to use a solid agrochemical active ingredient in the form of a liquefied material.

The temperatures can be varied over a certain range when carrying out the method according to the invention. Generally, work is carried out at temperatures between 0° C. and 80° C., preferably between 10° C. and 60° C.

When carrying out the method according to the invention, the procedure is generally such that the penetration promoter is mixed with one or more active ingredients and, if necessary, with additives, the emulsion stabiliser/crystallisation inhibitor and γ-butyrolactone. The components can be mixed together in any order. In a preferred variation, the procedure is such, however, that the emulsion stabiliser/crystallisation inhibitor Synperonic T/304® is mixed with one or more agrochemical active ingredients as well as with other additives, and the resulting pre-mix is dispersed in water in order to obtain emulsions, suspensions or solutions.

Equipment that is commonly used for the production of agrochemical formulations is suitable for carrying out the method according to the invention.

The agrochemical formulations according to the invention can be deployed in the forms commonly used for liquid preparations either as such or after previous dilution with water, hence, for example, as emulsions, suspensions or solutions. Application is carried out by the usual methods, i.e. by spraying, pouring or injection, for example.

The amount used of agrochemical formulations according to the invention can be varied over a larger range. This depends on the respective agrochemical active ingredients and their concentration in the formulations.

With the help of the formulations according to the invention, agrochemical active ingredients can be deployed on plants and/or on their habitat in a particularly advantageous manner.

At the same time, the tendency of solid active ingredients to crystallise in the spray liquor is considerably reduced, which guarantees trouble-free application.

The invention is illustrated by the following examples. The invention is not limited to the examples, however.

PRODUCTION EXAMPLES

The following table explains the components used in the examples.

| % w/w | Chemical description of component | Function | Supplier |
|---|---|---|---|
| 5-15 | Fluoxastrobin | Active ingredient | Bayer CropScience AG |
| 5-20 | Prothioconazole | Active ingredient | Bayer CropScience AG |
| 0-10 | Trifloxystrobin | Active ingredient | Bayer CropScience AG |
| 10-25 | 2-Ethyl hexanol alkoxylate | Penetration promoter | Bayer AG |
| 10-25 | Tristyrylphenol alkoxylate | Emulsifier | Bayer AG |
| 5-15 | Synperonic T/304 ® | Emulsion stabiliser/crystallisation inhibitor Ethylene diamine alkoxylate | Uniqema |
| 0-2 | Citric acid monohydrate or non-aqueous citric acid | pH stabiliser | |
| 0-0.1 | Fluowet PL 80 ® | Anti-foaming agent | Clariant GmbH |
| 20-70 | δ-butyrolactone | Solvent | |

Example 1

A mixture consisting of

| | |
|---|---|
| 8.7 g | Fluoxastrobin |
| 8.7 g | Prothioconazole |
| 15 g | 2-Ethyl hexanol alkoxylate |
| 15 g | Tristyrylphenol-ethoxy-propoxylate |
| 5 g | Tristyrylphenol ethoxylate |
| 10 g | Synperonic T/304 ® and |
| 37.6 g | δ-butyrolactone | was mixed and the resulting pre-mix dispersed in water in order to obtain an emulsion. The crystallisation of the product from the spray liquor was observed and compared.

Example 2

A mixture consisting of

| | |
|---|---|
| 6.5 g | Fluoxastrobin |
| 6.5 g | Trifloxystrobin |
| 12.9 g | Prothioconazole |
| 12 g | 2-Ethyl hexanol alkoxylate |
| 12 g | Tristyrylphenol-ethoxy-propoxylate |
| 4.5 g | Tristyrylphenol ethoxylate |
| 8 g | Synperonic T/304 ® and |
| 37.6 g | δ-butyrolactone | was mixed and the resulting pre-mix dispersed in water in order to obtain an emulsion.

Example 3 (Comparative Example)

A mixture consisting of

| | |
|---|---|
| 8.7 g | Fluoxastrobin |
| 8.7 g | Prothioconazole |
| 15 g | 2-Ethyl hexanol alkoxylate |

-continued

| | |
|---|---|
| 15 g | Tristyrylphenol-ethoxy-propoxylate |
| 5 g | Tristyrylphenol ethoxylate |
| 47.6 g | δ-butyrolactone | was mixed and the resulting pre-mix dispersed in water in order to obtain an emulsion. The crystallisation of the product from the spray liquor was observed and compared.

Crystallisation Test/Application Test

The application characteristics of the formulations can be checked in commercially available field sprays with different filter/nozzle combinations.

For this purpose, the formulations are diluted with water in the tank of the field spray, thus forming the so-called spray liquor, in this case an emulsion. 1.5 liters of the emulsion concentrate of the formulations according to the invention are diluted with 200 liters of water.

The spray liquors so obtained are sprayed until the spray tank is completely empty. This application is then carried out a total of twelve times in succession.

The spray liquor is allowed to stand without stirring for 24 hours between the 5th and 6th application, and for 72 hours between the 9th and 10th application. After the 12th application, the filters and nozzles of the field spray are removed and checked for possible sedimentation and blockages.

Crystallisation Test/Application Test with Example 1

After 12 applications (12 times 1.5 l formulation+200 l water), without intermediate cleaning of the spray tank, the formulation according to the invention of Example 1 showed a maximum filter coating of up to 10% with an 80 mesh nozzle filter, and ca. 1% with a 50 mesh nozzle filter.

Crystallisation Test/Application Test with Example 3

With the same application test with the field spray, after the 12th application, the formulation according to the invention of Example 3 showed a maximum filter coating of up to 90% with an 80 mesh nozzle filter, and ca. 25% with a 50 mesh nozzle filter.

Nozzle filter coatings of this kind already mean a significant curtailment in the application of spray liquor. With these filter coatings before the spray nozzle, the spray pattern (angle with which the spray mist emerges from the spray nozzle) collapses, and a complete blockage of the nozzle filter is imminent, so that no more product will be able to emerge from the spray nozzle. On the other hand, the formulation according to the invention of Example 1 shows no curtailment whatsoever.

The invention claimed is:

1. A formulation comprising:

a) 1-40 w/w % fluoxastrobin,

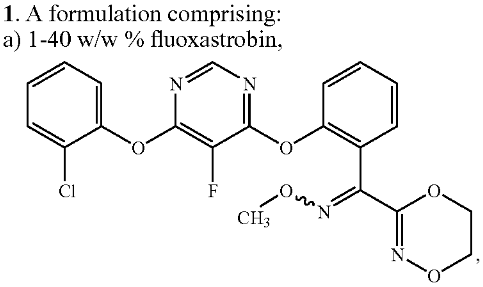

, b) 5-30 w/w % emulsifier, c) optionally a penetration promoter, and d) optionally additives, wherein the formulation contains 20-70 w/w % γ-butyrolactone and 5-20 w/w % of at least one ethylene diamine alkoxylate, which acts as an emulsion stabilizer or a crystallization inhibitor, or both.

2. The formulation according to claim 1, wherein the formulation contains an ethylene diamine alkoxylate of the formula

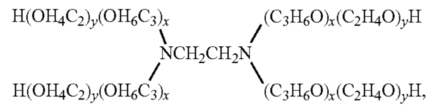

, wherein x and y are both 4.

3. The formulation according to claim 1 or 2, further comprising Prothioconazole

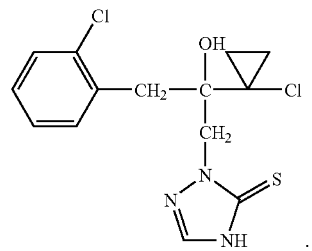

.

4. The formulation according to claim 1 or 2, further comprising Trifloxystrobin

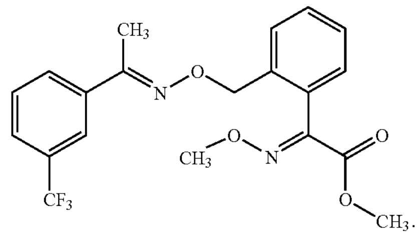

.

5. A method for producing the formulation according to claim 1, comprising mixing a) 1-40 w/w % fluoxastrobin,

, b) 5-30 w/w % emulsifier, c) optionally a penetration promoter, and d) optionally additives, e) 20-70 w/w % γ-butyrolactone, and f) 5-20 w/w % of an emulsion stabilizer or a crystallization inhibitor, or both.

6. A method of plant protection comprising contacting an effective amount of an agrochemical formulation according to claim 1 to a plant or a plant habitat, or both.

* * * * *

UNITED STATES PATENT AND TRADEMARK OFFICE
CERTIFICATE OF CORRECTION

PATENT NO. : 7,655,599 B2  Page 1 of 1
APPLICATION NO. : 10/563328
DATED : February 2, 2010
INVENTOR(S) : Rochling et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 673 days.

Signed and Sealed this

Twenty-third Day of November, 2010

David J. Kappos
*Director of the United States Patent and Trademark Office*